(12) United States Patent
Radmer et al.

(10) Patent No.: US 8,444,606 B2
(45) Date of Patent: May 21, 2013

(54) INJECTION DEVICE

(75) Inventors: Bo Radmer, Hillerød (DK); Claus Schmidt Moller, Fredensborg (DK); Lars Morch Groth, Fredensborg (DK); Klaus Thogersen, Charlottenlund (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/618,318

(22) Filed: Nov. 13, 2009

(65) Prior Publication Data

US 2010/0179485 A1 Jul. 15, 2010

Related U.S. Application Data

(63) Continuation of application No. 11/791,397, filed as application No. PCT/EP2005/056313 on Nov. 29, 2005, now abandoned.

(60) Provisional application No. 60/647,837, filed on Jan. 28, 2005.

(30) Foreign Application Priority Data

| Dec. 1, 2004 | (DK) | 2004 01881 |
| Jan. 21, 2005 | (EP) | 05001213 |
| Aug. 19, 2005 | (DK) | 2005 01168 |

(51) Int. Cl.
*A61M 5/00* (2006.01)

(52) U.S. Cl.
USPC ........... 604/211; 604/207; 604/208; 604/209; 604/210

(58) Field of Classification Search
USPC ................................. 604/207–211
See application file for complete search history.

(56) References Cited

U.S. PATENT DOCUMENTS

| 3,905,366 A | 9/1975 | Callahan et al. |
| 5,320,609 A | 6/1994 | Haber et al. |
| 5,342,320 A | 8/1994 | Cameron |
| 6,004,297 A | 12/1999 | Steenfeldt-Jensen et al. |
| 6,048,336 A | 4/2000 | Gabriel |

(Continued)

FOREIGN PATENT DOCUMENTS

| DE | 29703820 | 8/1998 |
| DE | 29724186 | 5/2000 |

(Continued)

OTHER PUBLICATIONS

Ypsopen Leaflet Standard Cartridge (Opposition EP1827538 Dated May 7, 2010; Haselmeier/Novo Nordisk).

(Continued)

*Primary Examiner* — Bhisma Mehta
*Assistant Examiner* — Larry R Wilson
(74) *Attorney, Agent, or Firm* — Marc A. Began

(57) ABSTRACT

The invention concerns an injection device for apportioning set doses of a drug from a reservoir to a subject. The injection device comprises a housing having an interior thread formed as an outwardly pointing thread carried on an upstanding tower centrally located in the pen shaped device. This outwardly pointing thread forms a first thread connection with the interior thread of the rotatable scale drum. The injection device further comprises a driver for moving the piston rod forward when moved axially. The driver operates the piston rod through a second thread connection having a pitch different than the first thread connection.

1 Claim, 17 Drawing Sheets

U.S. PATENT DOCUMENTS

| | | | |
|---|---|---|---|
| 6,161,731 A | 12/2000 | Sigg | |
| 6,221,053 B1 * | 4/2001 | Walters et al. | 604/211 |
| 6,228,067 B1 * | 5/2001 | Gabriel | 604/211 |
| 7,291,132 B2 | 11/2007 | DeRuntz et al. | |
| 2004/0000818 A1 | 1/2004 | Preuthun et al. | |

FOREIGN PATENT DOCUMENTS

| | | |
|---|---|---|
| DE | 10302163 | 7/2004 |
| EP | 554995 | 8/1993 |
| EP | 1000631 | 7/2002 |
| EP | 1645301 | 4/2006 |
| FR | 2684880 | 6/1993 |
| WO | WO93/11813 | 6/1993 |
| WO | 94/03392 A1 | 2/1994 |
| WO | 95/31235 A1 | 11/1995 |
| WO | WO98/39041 | 9/1998 |
| WO | WO 03/075985 | 9/2003 |
| WO | WO 2004/002557 | 1/2004 |
| WO | WO 2004/078241 | 9/2004 |

OTHER PUBLICATIONS

English Abstract of EP1000631.
Din ISO Pen-Systems—Part 1: Glass Cylinders for Pen-Injectors for Medical Use (ISO 13926-1:2004), Text in German and English 2005.
ISO Pen-Injectors for Medical Use—Part 1: Pen-Injectors—Requirements and Test Methods 2000 1$^{st}$ Ed 12-15.

* cited by examiner

INJECTION DEVICE

CROSS-REFERENCE TO RELATED APPLICATIONS

This application is a continuation application of U.S. patent application Ser. No. 11/791,397, filed May 23, 2007, which is a 35 U.S.C. §371 national stage application of International Patent Application PCT/EP2005/056313 (published as WO 2006/058883), filed Nov. 29, 2005, which claimed priority of Danish Patent Application PA 2004 01881, filed Dec. 1, 2004, European Patent Application 05001213.7, filed Jan. 21, 2005 and Danish Patent Application PA 2005 01168, filed Aug. 19, 2005; this application further claims priority under 35 U.S.C. §119 of U.S. Provisional Application 60/647,837, filed Jan. 28, 2005.

THE TECHNICAL FIELD OF THE INVENTION

The invention relates to an apparatus such as an injection pen for delivering a drug to the human body preferably in a subcutaneous way and especially to a user energized injection pen having a rotatable scale drum.

DESCRIPTION OF RELATED ART

In the disclosure of the present invention reference is mainly made to the treatment of diabetes by injection of insulin; however this is only an exemplary use of the present invention.

Injection pens are mainly made for users who have to inject themselves frequently, e.g. people suffering from diabetes. A number of demands are set to such injection pens. The setting of a dose must be easy an unambiguous and it must be easy to read the set dose. It must be possible with a minimum of trouble to cancel or change a wrongly set dose and when the dose is injected the dose setting must return to zero. When a prefilled injection pen is in question, i.e. an injection pen which is disposed of when the reservoir is empty, the injection pen must further be cheap and made of materials suitable for recycling.

Most dose setting devices work with a threaded piston rod co-operating with a nut where the nut and the piston rod may be rotated relative to each other. The dose setting may be obtained by screwing the nut away from a stop to which it is return during injection by pressing the piston rod forward until the nut member abuts the stop. By other dose setting devices one of the elements, the nut or the piston rod, is kept inrotatable and the other is allowed to rotate a set angle depending on the set dose, whereby the piston rod is screwed forward a distance through the nut member.

A prior art delivery apparatus is disclosed in U.S. Pat. No. 6,004,297. The apparatus disclosed in FIGS. 6 to 10 comprises a scale drum having an exterior thread which is guided in a helical thread provided on the inside of the outer wall of the housing. The scale drum is axially coupled to the driver to follow the axial movement of the driver. The driver further has an interior thread which engages a proximal thread on the piston rod such that when the driver is moved axially forward in the pen, the piston rod is rotated and henceforth screwed forward in the thread connection between the piston rod and the wall of the housing.

The tolerances in the thread connection between the scale drum and the housing is decisive for the precision of the display. If the scale drum e.g. were a little loose in the thread connection an erroneous dose size could be displayed, however if it were too tight in the thread connection, it would be difficult to press back the dose setting knob.

A similar injection pen is disclosed in WO 04/078241. This injection pen comprises a threaded piston rod which is screwed forward in an internal threaded nut when rotated. A drive sleeve having a thread mating the thread of the piston rod rotates the piston rod when moved axially forward. The drive sleeve is releasable coupled to a dose dial sleeve which is rotated to dial up a dose. The dose dial sleeve is rotated out from the housing in order to set up a dose and it is rotated back to release the set dose. The drive sleeve is rotated together with the dose dial sleeve when a dose is set but prevented from rotation when the set dose is injected. When the dose dial sleeve is rotated back, the user must be sure that the dose dial sleeve is free to rotate as any obstacle for the rotation will increase the pressure needed to press back the dose dial sleeve.

Some drugs, such as insulin are self-administered, and the typical diabetes person will require subcutaneous injections of insulin several times during the course of the day. In administering such an injection, the user, once the size of the dose has been set holds the injection pen in the palm of one hand while placing the thumb finger on the back-end of the push button. When a large dose has been set, the distance from the device itself to the push button is considerable thereby making it difficult for people with small hands or reduced dexterity to reach behind the push button.

Since most injections of these drugs are performed in private surroundings by the user himself there is a great desire for very simple yet also very precise injection devices having a very precise dose reading combined with a small displacement of the push button even when setting large doses.

DESCRIPTION OF THE INVENTION

Having regard to the above-identified prior art devices, it is an object of an embodiment of the present invention to provide a drug delivery device which eliminates disadvantages in the prior art drug delivery device. It is especially an object to provide a drug delivery device having a reduced displacement of the push button and a reduced friction making the drug delivery device more user friendly. Further it is an object to provide an injection device were all rotating parts are encapsulated.

By surrounding the dose indication sleeve with a shield, it is secured, in one embodiment of the invention, that the user does not touch the scale drum during operation. In any device, the scale drum must be rotatable in order to display the set dose. When the scale drum is encapsulated inside a shield which at the same time can be used to transfer pressure from the injection button, the injection device can be made considerable shorter than known devices were the dose drum is encapsulated in the housing of the injection device. In order for a user to visible see the scale indication drum, the shield must be made such that the user can view the scale drum e.g. by providing a longitudinal opening in the shield which opening is aligned with the window in the housing of the injection device.

In an embodiment of the present invention, the shield could alternatively be made with a longitudinal transparent area through which transparent area the indications on the scale drum can be viewed. The shield could also be made fully transparent which is preferred if the shield rotates. The transparent or partly transparent shield can be made cylinder-shaped to surround the scale drum, or at least a part of the scale drum. This allows the scale drum to climb out of the housing yet being untouchable.

The drive sleeve is in an exemplary embodiment able to be coupled and uncoupled from the shield. If the dose setting and injection mechanism is the kind were the driver during injection is brought axially back to its initiate position in order to force the piston rod to rotate, the driver can be rotational locked to the shield during injection such that both the shield and the driver is moved axially. This permits the scale drum to rotate back to its initiate position inside the shield without being touched by the user.

Depending on the embodiment of the present invention, the shield is either axially guided in the housing or free to rotate relative to the housing. If the shield is free to rotate it can preferable be rotational locked e.g. by moulding to the push button so as to form one common dose setting member. If the shield is axially guided in the housing the preferred way is to guide the shield in a longitudinal track in the housing.

Correspondingly, an injection device may be provided according to an embodiment of the present invention where the drive sleeve is associated with a first thread and releasable connected to the dose setting member such that the drive sleeve can be connected or disconnected from the dose setting member.

Further, the dose indication sleeve can be associated with a second thread having a pitch different from the first thread and releasable connected to the dose setting member such that the dose indication sleeve can be connected or disconnected from the dose indication sleeve.

This results in the four following different engagements:
Dose setting member connected to both drive sleeve and dose indication sleeve,
Dose setting member disconnected from both drive sleeve and dose indication sleeve,
Dose setting member connected to the drive sleeve but disconnected from the dose indication sleeve,
Dose setting member disconnected from the drive sleeve but connected to the dose indication sleeve.

During dose setting, one engagement can be utilized while during expelling of the dose a different engagement can be utilized.

At the same time, the drive sleeve can be guided in one thread connection having one pitch and the dose indication sleeve in a different thread connection having a different pith such that the drive sleeve and the dose indication sleeve can be rotated with different rotational speeds.

In accordance with a particular embodiment of the present invention, when setting a dose the dose setting member is disconnected from the drive sleeve and connected to the dose indication sleeve such that when rotating the dose setting member, the dose indication sleeve is screwed up the second thread at a speed determined by the pitch of the second thread.

If the drive sleeve is axially coupled to the dose setting member and the dose indication sleeve it will be dragged along and forced to rotate in the first thread at a speed determined by pitch of the first speed.

When injecting or otherwise expelling the set dose, the dose setting member is connected to the drive member and disconnected from dose indication sleeve such that an axial pressure applied to the dose setting member will be transformed to an axial movement of drive sleeve while the disconnected dose indication scale will be screwed back in the second thread.

In a particular embodiment of the invention, the pitch of the first thread is decisive for ratio of the translation of the longitudinal movement of the drive sleeve to the rotational movement of the piston rod, and the pitch of the second thread is decisive for the ratio of the translation of the longitudinal movement of the dose indication sleeve and the rotational movement of the dose indication sleeve.

According to an example of the invention, the first thread has a pitch larger than the pitch of the second thread. A result of this is that the dose indication sleeve rotates more than one revolution for each revolution the drive sleeve is rotated.

In one embodiment of the invention, when setting a dose the dose indication member and the dose setting member is screwed up the second thread having the smaller pitch such that the distance the dose setting member grows out from the proximal end of the injection device for each dose indication printed on the dose indication sleeve is reduced.

In a preferred embodiment of the invention, during injection the drive sleeve must be moved axially without any rotation in order to make sure the set dose is correctly expelled.

This can be accomplished by preventing the drive sleeve from rotating relatively to the housing.

A preferred way of doing is by locking the drive shield to a shield which is guided in a longitudinal track in the housing.

Since the shield is located on the outside of scale indication sleeve it preferably should be at least partly transparent such that the user can view the dose indication sleeve through the shield.

In an embodiment the axially movable shield prevents the user from physical contact with the rotating scale indication sleeve.

In an embodiment of the present invention, when setting up a dose to be expelled, the dose setting member is rotational connected to the dose indication sleeve. The drive sleeve which is disconnected from the dose setting member is supported by the dose indication sleeve such that it follows the axial movement of the dose setting member and the dose indication sleeve. By doing so the drive sleeve is screwed up its thread connection.

The thread in which the drive sleeve engages is the first thread which may be provided on the piston rod guide which again is keyed to the piston rod such that the piston rod rotates with the piston rod guide.

In an alternative embodiment, the drive sleeve can engage directly in a thread provided on the piston rod.

In one embodiment, the second thread which is engaged by the dose indication sleeve is provided on a thread tower which is centrally provided in the housing. This thread tower can either be a loose insert which is rotational connected to housing or it can be moulded integrally with the housing.

DEFINITIONS

An "injection pen" as in this application is typically a mechanical i.e. user energized injection apparatus having an oblong or elongated shape somewhat like a pen for writing. Although such pens usually have a tubular cross-section, they could easily have a different cross-section such as triangular, rectangular or square.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Elements having the same function in the different examples disclosed are preferably numbered with the same number carrying the number of the example in the beginning. The piston rod is e.g. referred to as number 120 in example one and as number 6120 in example six.

Figure 1:
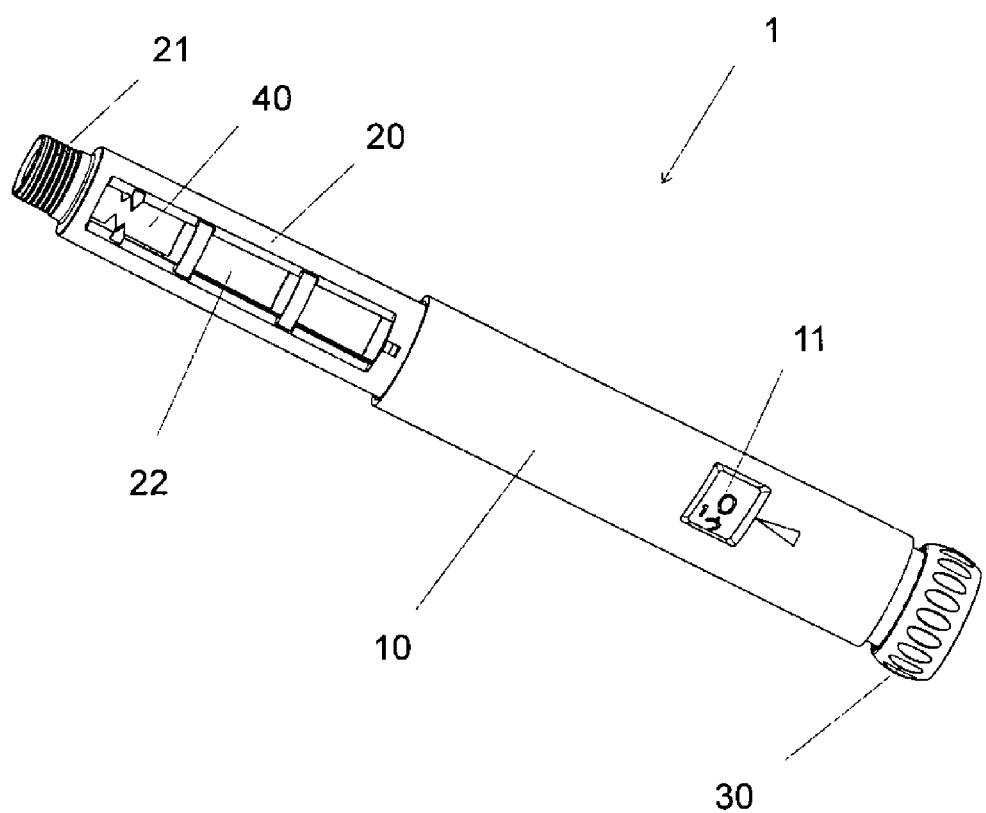
FIG. 1 shows a perspective view of the injection device.

FIG. 1 discloses a user energized injection pen 1 comprising a housing 10 and a cartridge holder 20. The housing 10 is provided with a window 11 through which the dose set by rotating the push button 30 can be viewed. The cartridge holder 20 is at its distal end provided with a thread 21 for securing a not shown injection needle to the injection pen 1. The cartridge holder 20 is further provided with a longitudinal opening 22 through which a user can inspect the drug contained in the cartridge 40 embedded in the cartridge holder 20.

The interior of the injection pen is detailed disclosed in the FIGS. 2 to 5.

The push button 30 is disposed at the proximal end of the injection device 1 and connected to a dose setting member 50 by a plurality of inwardly pointing locking protrusions 51 on the proximal end of the dose setting member 50 entering depressions 31 in the proximal end of the push button 30. This prevents rotation between the push button 30 and the dose setting member 50. The two parts; push button 30 and dose setting member 50 could be coupled together in a number of alternative ways e.g. through welding or gluing as long they are rotational locked to each other.

The push button 30 can further be provided with a colour indication e.g. for indicating the type of insulin in the injection device 1. Such colour indication can be made as an insert in the push button 30.

A shield 60 is axially slidable mounted to the housing 10. The shield 60 is provided with a protrusion 61 sliding in a longitudinal track 12 provided on the inside surface of the housing 10. The shield 60 is thereby rotational locked to the housing 10 i.e. prevented from rotating relatively to the housing 10. The shield 60 is further provided with a plurality of radial shield teeth 62 at the proximal end which shield teeth 62 interacts with a corresponding rim of push button slits 32 thereby allowing the push button 30 to rotate relatively to the shield 60 with a clicking sound. When axial pressure is applied to the push button 30, the shield teeth 62 abut the ends of the push button slits 32 thereby locking the push button 30 rotational to the shield 60.

The dose setting member 50 is at its distal end coupled to a drive sleeve 70. This drive sleeve 70 has on the outside surface a number of helical formed resilient arms 71 which at there connection points ends in toothed surfaces 72 pointing in the proximal direction. These toothed surfaces 72 interacts with a dose setting member toothed rim 52 provided at the distal end of the dose setting member 50 when the dose setting member 50 and the drive sleeve 70 is pressed together.

The dose setting member 50 further comprises a plurality of dose setting member protrusions 53 which engage a toothed dose indication sleeve rim 91 (best seen in FIG. 2) located at the proximal end of the dose indication sleeve 90. The dose setting member protrusions 53 can be brought out of engagement with the toothed dose indication sleeve rim 91 by moving the dose setting member 50 axially relatively to the dose indication sleeve 90 a distance determined by the size of the dose setting member protrusions 53 and the toothed dose indication sleeve rim 91. The dose setting member protrusion 53 are kept in engagement with the toothed dose indication sleeve rim 91 by the resilient arms 71 on the drive sleeve 70 which urges the dose setting member 50 in the proximal direction.

Further the dose indication sleeve 90 is provided with a number of mounting openings 93 facilitating the insertion of the dose setting member 50 in the dose indication sleeve 90 when assembling the injection device 1.

At its distal end the dose indication sleeve 90 is provided with a male thread 92 engaging the female thread 101 of the thread member 100. This thread member 100 is centrally located in the housing 10 and rotational locked to the housing 10 by a number of thread member protrusions 102 engaging longitudinal tracks 12 provided on the inside surface of the housing 10.

Figure 2:
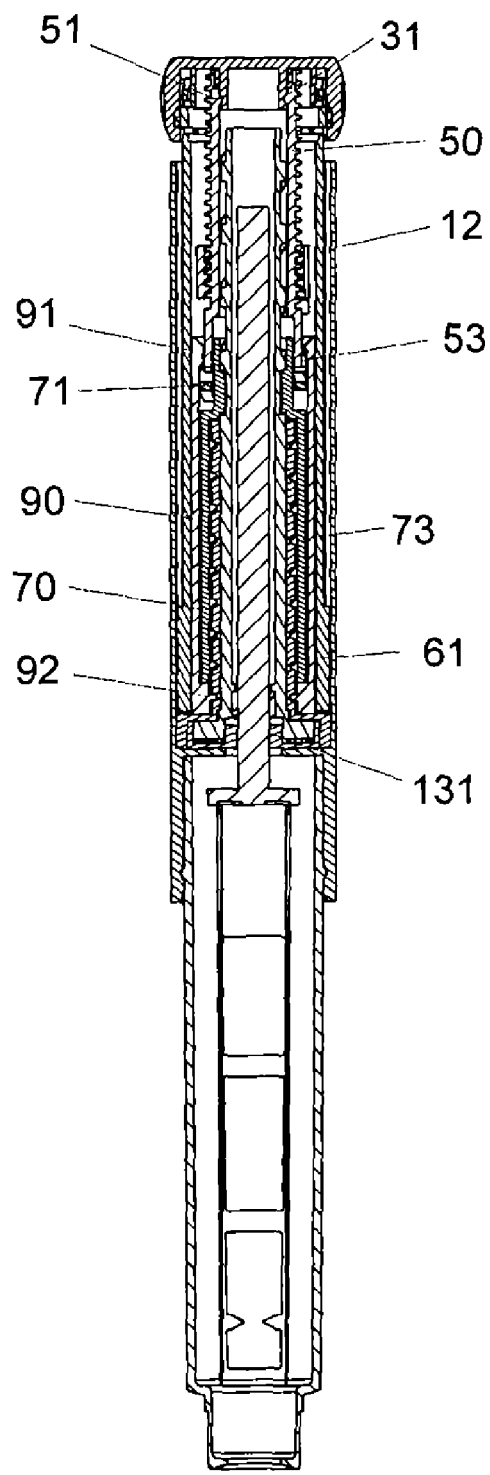
FIG. 2 shows a sectional view of the injection device of FIG. 1 with no dose set.

Internally the thread member 100 supports the piston rod guide 110. The piston rod guide 110 has a circular outer surface 111 supporting the thread member 100 and an outer threaded surface 112 engaging the drive sleeve 70 in its internal drive thread 73 (as best seen in FIG. 2).

The piston rod guide 110 has an internal thread 113 mating the thread 122 on the piston rod 120.

The piston rod 120 which is centrally located in the housing 10 has a circular outer surface with a number of keys 121 and a thread 122. A piston foot 123 for transferring pressure to a not shown resilient piston inside the cartridge 40 is located at the distal end of the piston rod 120.

Figure 3:
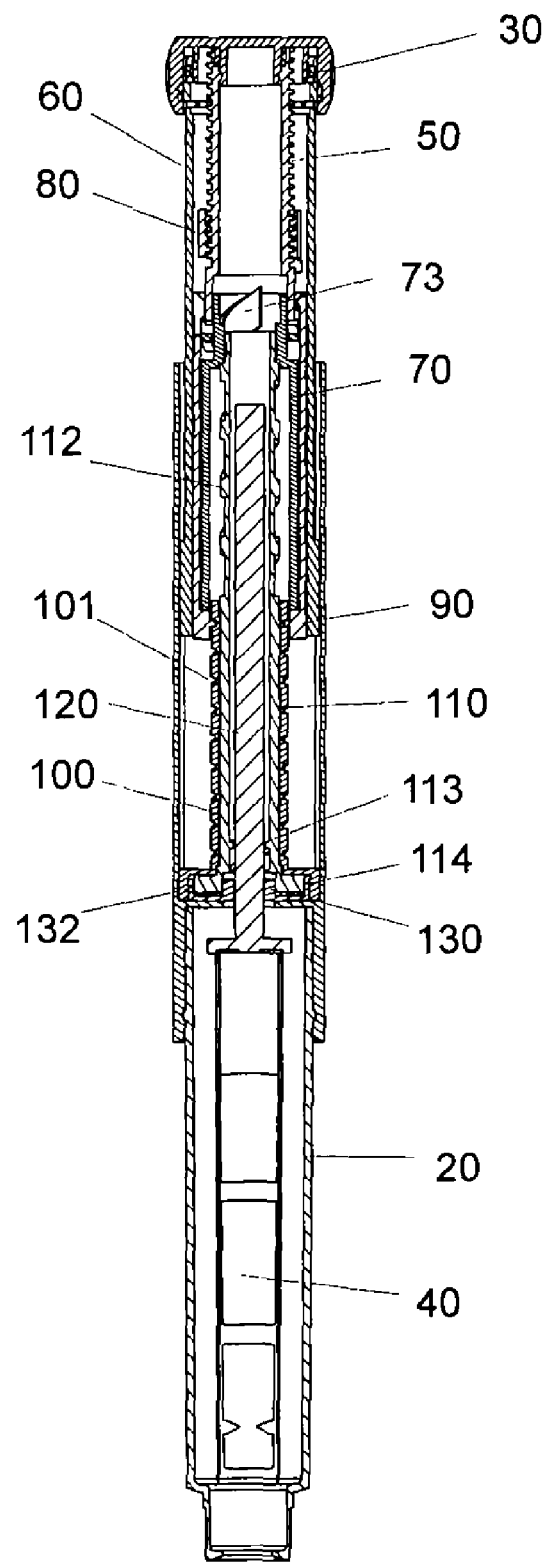
FIG. 3 shows a sectional view of the injection device of FIG. 1 with a dose set.
Figure 4:
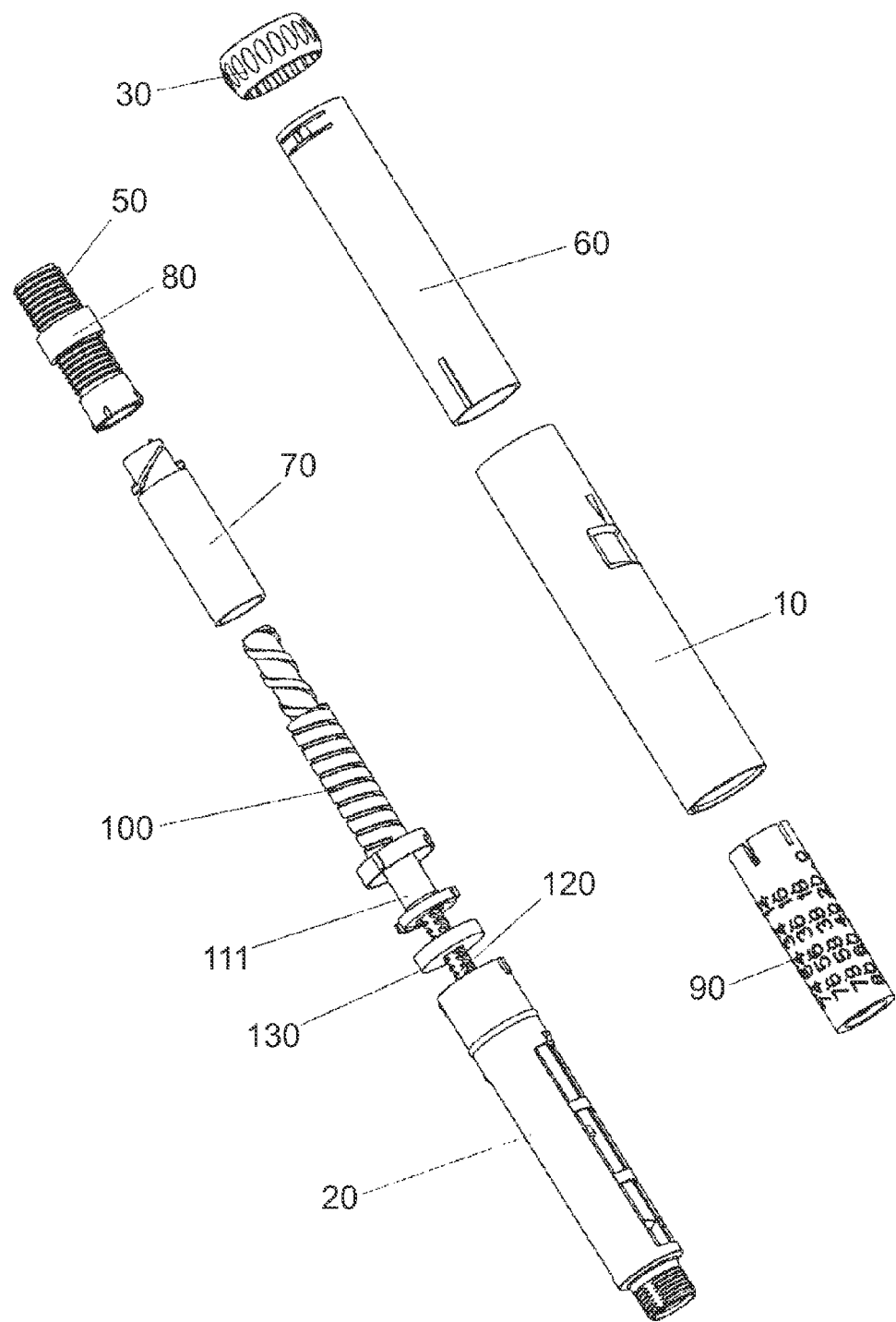
FIG. 4 shows a partly exploded view of the injection device.
Figure 5:
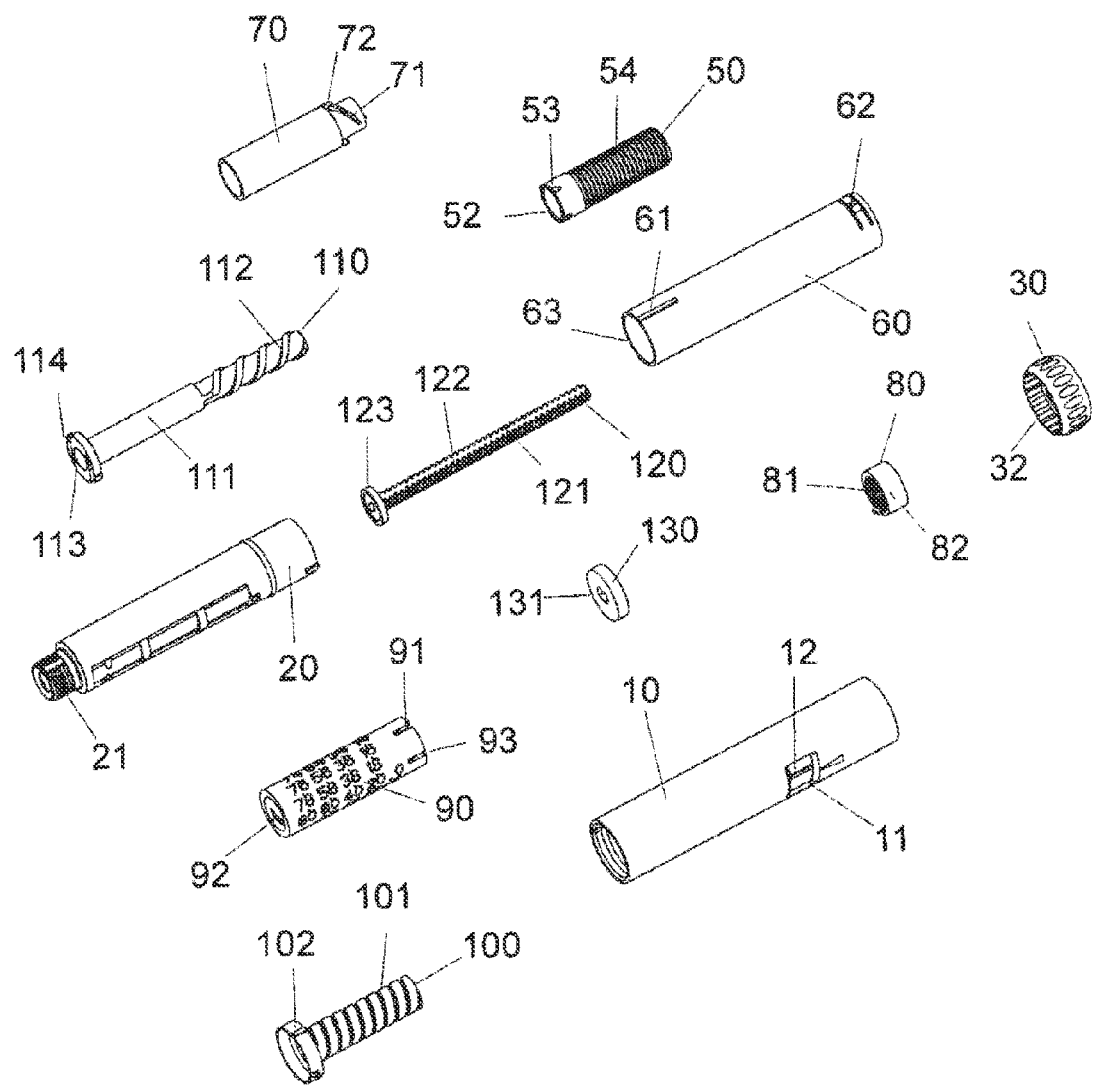
FIG. 5 shows a perspective view of the parts presented in FIG. 4.

A dish 130 is clicked into the distal end of the thread member 100. The dish 130 has a centrally located keyed opening 131 mating the key 121 of the piston rod. Further the dish 130, as best seen in FIG. 3, has a plurality of inwardly pointing teeth 132 engaging the pawls 114 of the piston rod guide 110 thereby securing that the piston rod guide 110 can only rotate in one direction relatively to thread member 100 and the housing 10. The allowed direction being one that moves the piston rod 120 forward in the distal direction.

Rotation of the piston rod guide 110 and thereby the internal thread 113 will screw the piston rod 120 forward through the dish 130 due to the fact that the dish 130 through its connection to the thread member 100 is rotational locked to the housing 10

To set a dose, the dose setting member 50 is rotated by rotating the push button 30 which is connected to the dose setting member 50. This rotating is transmitted to the scale indication sleeve 90 through the engagement between the dose setting member protrusions 53 and the toothed dose indication sleeve rim 91.

During this rotation the scale indication sleeve 90 rotates up the thread 101 on the thread member 100. At the same time it moves the drive sleeve 70 in the proximal direction since the drive sleeve 70 rest on the scale indication sleeve 90. The drive sleeve 70 is henceforth screwed up the thread 112 on the piston rod guide 110.

The pitch on the threaded surface 112 of the piston rod guide 110 is preferably different from the thread 101 on the thread member 100, and the piston rod guide 110 preferably has the largest pitch.

If e.g. the ration between the pitches of the threaded surface 112 of the piston rod guide 110 and the thread 101 of the threaded member is 2 to 1 with the pitch of the threaded surface of the piston rod guide 110 being the largest. Then when e.g. rotating the dose indication sleeve 90 four full revolutions up the thread 101 of the thread member 100, the drive sleeve 70 will only be rotated two revolutions up the thread 112 on the piston rod guide 112. This provides room for increasing the distance between the not shown indications on the dose indication sleeve 90 while at the same time keeping the distance the push button grows out from the housing 10 at a minimum.

Upon rotation of the dose setting member 50 in the dose setting direction, the shield 60 is moved axially out of the housing 10 as the shield 60 abuts the scale indication sleeve 90 and is guided in the track 12.

If the user wants to decrease the set dose, he rotates the dose setting member 50 in the opposite direction whereby the dose indication sleeve 90 is screwed down the thread 101 of the thread member 100.

The shield 60 is at least partially transparent such that the user can see the indications printed on the outside surface of the scale indication sleeve 90 through the shield 60. Since the shield 60 is axially guided in the housing, the transparent part only needs to be the part of the shield 60 passing past the window 11. Further instead of being partly or fully transparent, the shield 60 could comprise a longitudinal opening through which the scale indication sleeve 90 can be viewed. The shield 60 needs not cover the scale drum in its entire length. The shield 60 must however protect the part of the scale indication sleeve 90 that is outside the boundaries of the housing (10) when the set dose is injected such that the user does not apply a sideways pressure on the scale indication drum 90 when it rotates back to its initial position.

To inject a dose, the dose setting member 50 is moved in distal direction by pressing the push button 30 back towards the housing 10. Such axial movement locks the push button 30 to the shield 60 and it moves the dose setting member protrusions 53 out of engagement with the toothed dose indication sleeve rim 91 thereby allowing the dose indication sleeve 90 to rotate down the thread 101 on the threaded member 100. At the same time the dose setting member 50 presses the resilient arms 71 down and abuts the toothed surface 52 which rotational locks the dose setting member 50 to the drive sleeve 70.

In this position continuously forward axial movement of the dose setting member 50 and the drive sleeve 70 forces the piston rod guide 110 to rotate due to the engagement between the internal drive thread 73 and the thread 112 of the piston rod guide 110 thereby rotating the piston rod guide 110 and screwing forward the piston rod 120.

End-of-Content Feature

A nut 80 is located over the dose setting member 50 and is in threaded contact with an exterior thread 54 on the dose setting member 50 through an internal thread 81. The nut 80 is at the same time inrotatable connected to the shield 60 by the protrusion 82 being guided in the longitudinal slot 63 located on the inside of the shield 60.

When a dose is set the dose setting member 50 is rotated relatively to the shield 60 and to the nut 80 bringing the nut 80 forward in the distal direction from a proximal starting point. The distance the nut 80 is brought forward relates to the size of dose being set.

When the set dose is injected, the nut 80 is moved axially forward the same distance as the dose setting member 50 and the shield 60. The position of the nut 80 on the exterior thread 54 therefore relates to the remaining content of drug in the reservoir.

When the nut 80 reaches the end of the thread 54, the nut 80 can be screwed no further and the dose setting member 50 in prohibited from further rotation. A more detailed description of such end-of-dose feature is provided in WO 01/019434 which is hereby incorporated by reference.

When the thread 54 is provided on the part that rotates with the slowest rotational speed which in this case is the dose setting member 50, the length of the thread 54 can be reduced since the nut 80 only moves a little distance in the thread 54. This is illustrated in the embodiment depictured in FIG. 9.

Further the end of the thread 54 can be made with a pitch different from the remaining part of the thread 54. If the thread is e.g. made larger in the end on the thread 54, the nut can be accelerated in the end of its run which could make room for a larger end surface in the thread 54.

Figure 6:
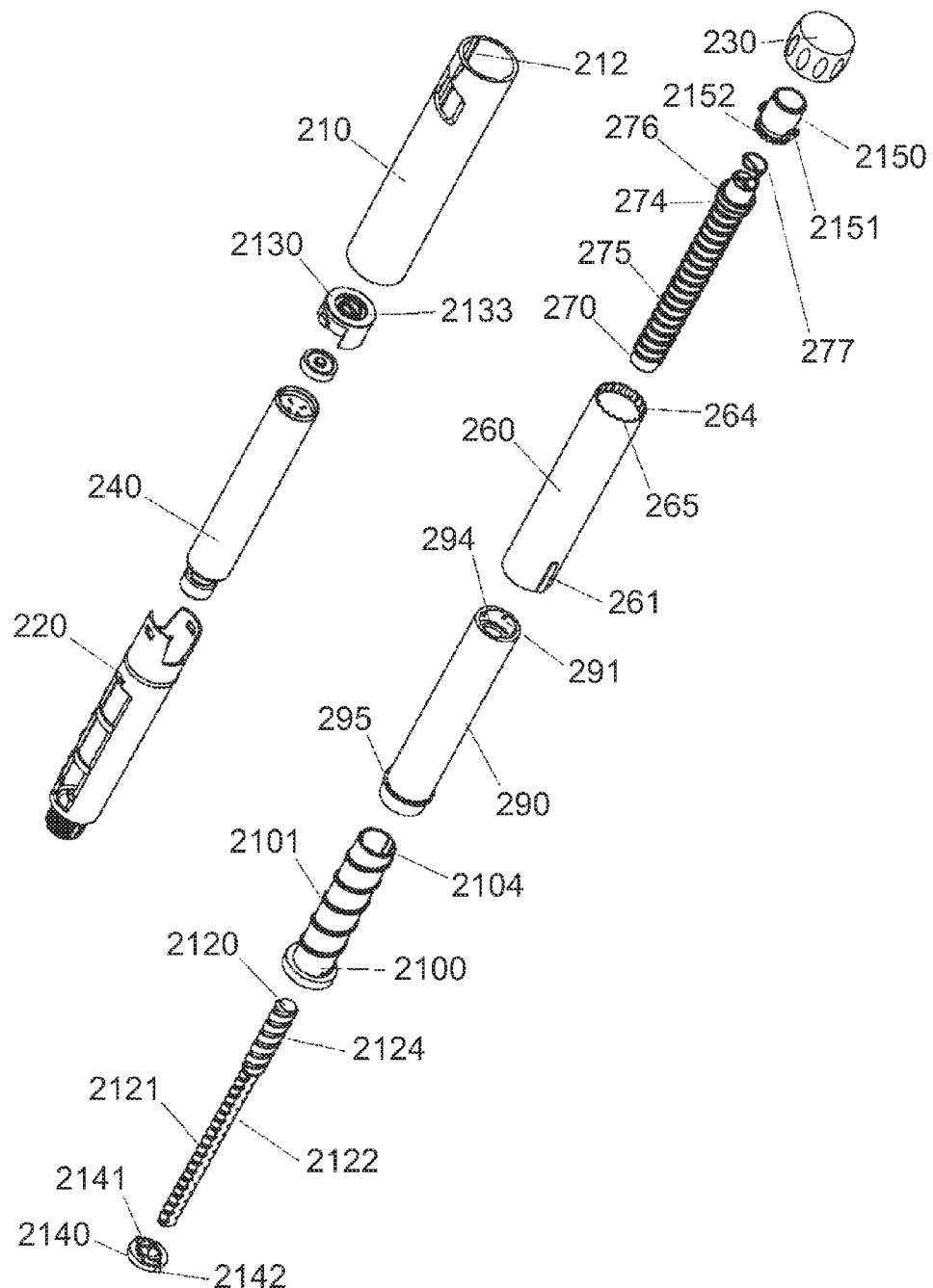
FIG. 6 shows a perspective view of a different example of an injection device.
Figure 7:
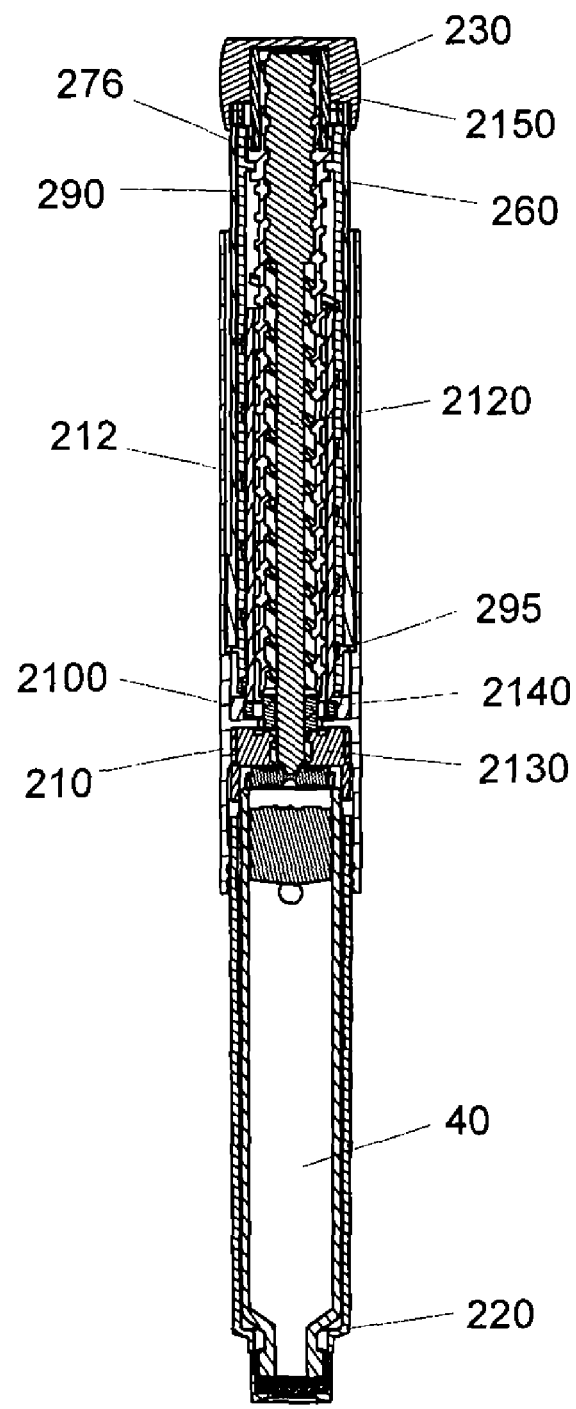
FIG. 7 shows a sectional view of the injection device of FIG. 6 with no dose set
Figure 8:
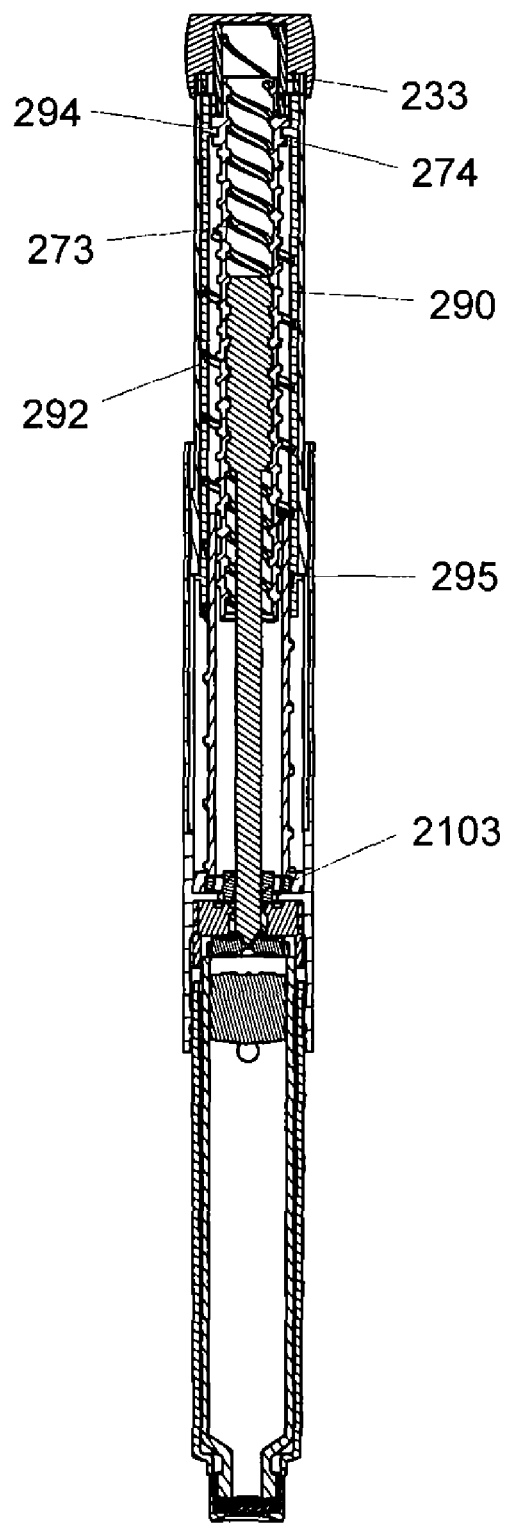
FIG. 8 shows a sectional view of the injection device of FIG. 6 with a dose set

Embodiment Disclosed in FIGS. 6 to 8

The push button 230 is firmly connected to a click element 2150 that follows the movement of the push button 230.

This click element 2150 is provided with resilient arms 2151 that engages a toothed ring 264 in the shield 260. Further a toothed ring 2152 engages a rim of teeth 291 on the dose indication sleeve 290.

The shield 260 is provided with a protrusion 261 guided in a longitudinal track 212 inside the housing 210.

Further the piston rod 2120 is provided with two threads 2122, 2124 having different pitches and where the distal thread 2122 has a keyed surface 2121 mating the key 2141 in the key element 2140. The distal thread 2122 mates the internal thread 2133 of a dish 2130 which is secured in the cartridge holder 220.

Whenever the piston rod 2120 is rotated it is screwed forward in the thread 2133. At the same time the key element 2140 secures that the piston rod 2120 can only rotate in one rotational direction due to the engagement between the resilient arms 2142 and the and an internal toothed ring 2103 provided on the thread member 2100 which is non-rotational fixed in the housing 210.

The proximal thread 2124 mates the internal thread 273 of the drive sleeve 270 which further has a single ring shaped track 274 engaging an inner ring shaped protrusion 294 on the dose indication sleeve 290 such that the drive sleeve 270 and the scale indication sleeve 290 axially moves together.

When setting a dose, the user rotates the push button 230. Due to the engagement between the protrusions 291 and the toothed ring 2152, the scale indication sleeve 290 follows the rotation of push button 230. In doing so, the scale indication sleeve 290 is by its inside thread 292 rotated up the thread 2101 on the thread member 2100.

The engagement between the ring shaped track 274 of the drive sleeve 270 and the inner ring shaped protrusion 294 of the scale indication sleeve 290 forces the drive sleeve 270 to follow the axial movement of the scale indication sleeve 290. During its axial movement, the drive sleeve 270 rotates on the thread 2124 which has a pitch different from the pitch of the thread 2101 such that the rotational speed of the drive sleeve 270 on one hand and the scale indication sleeve 290 and the push button 230 on the other hand are different.

The scale indication sleeve 290 is provided with an outer ring 295 on which the proximal end of the shield 260 rests such that the shield 260 is moved away from the injection device 201 when the drive sleeve 270 and the scale indication sleeve 290 is rotated.

In order to inject a dose, the user presses back the push button 230 against the force of the spring 277 whereby the teeth 233 on the push button 230 engages the teeth 265 at the proximal end of the shield 260 inrotatable locking the shield 260 and the push button 230 together. At the same time the drive sleeve 270 and the push button 230 is kept inrotatable by a ring of not shown teeth on the click element 2150 entering into engagement with a ring of corresponding teeth 276 on the drive sleeve 270.

The toothed ring 2152 on the click element 2150 moves out of engagement with the protrusions 291 on the dose indication sleeve 290 whereby the sleeve 290 is free to rotate. When the toothed ring 2152 is out of engagement with the protrusion 291 and further force is applied the axial forward movement of the drive sleeve 270 forces the piston rod 2120 to rotate as well as the dose indication sleeve 290 is also forced to rotate in its thread connection 2101, 292. The rotation of the piston rod 2120 screws the piston rod 2120 forward in the mating thread 2133 of the dish 2130.

A not shown EOC nut engages the longitudinal track 2104 in the thread member 2100 and the helical track 275 of the drive sleeve 270.

Figure 9:
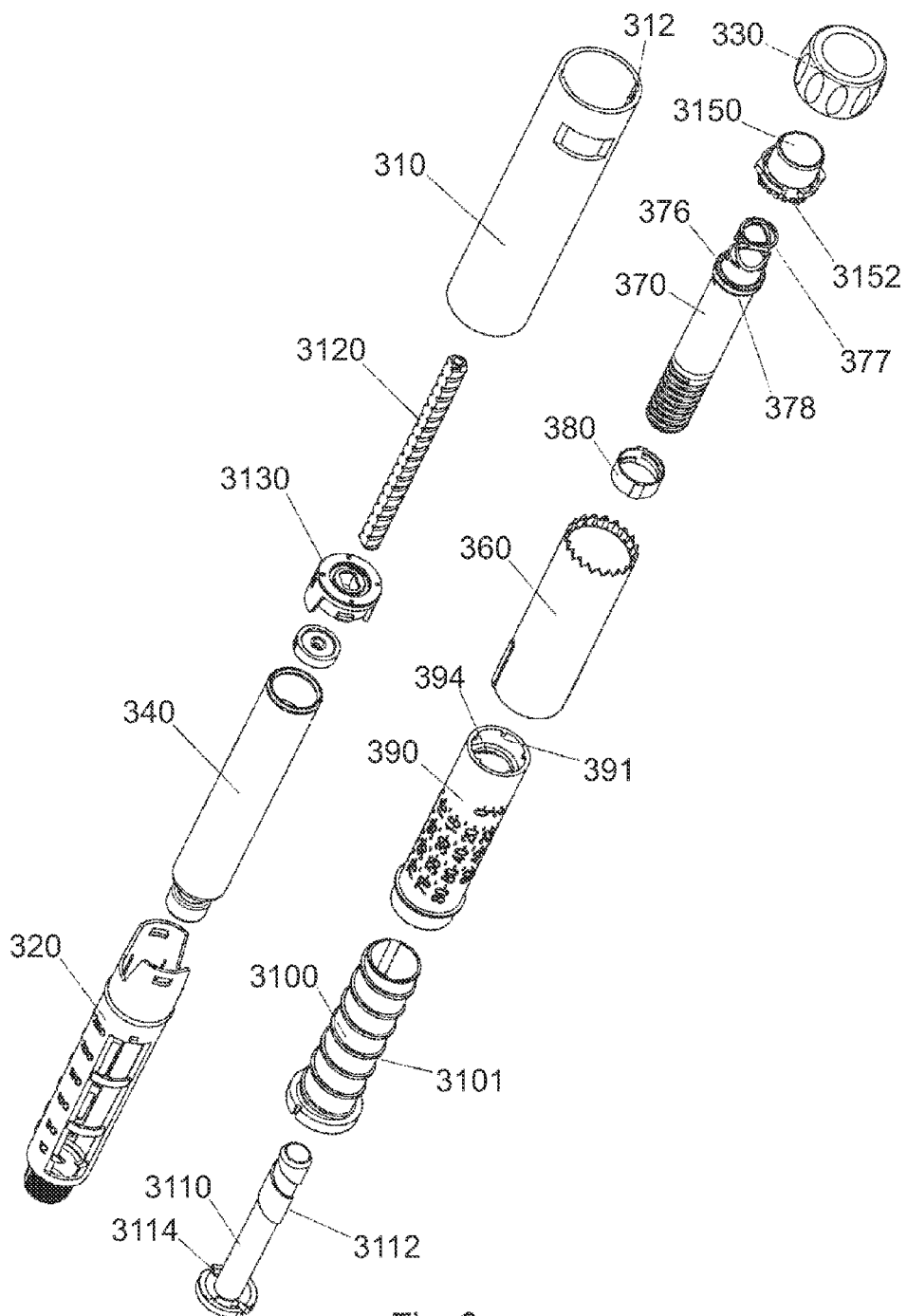
FIG. 9 shows a perspective view of another example of an injection device.
Figure 10:
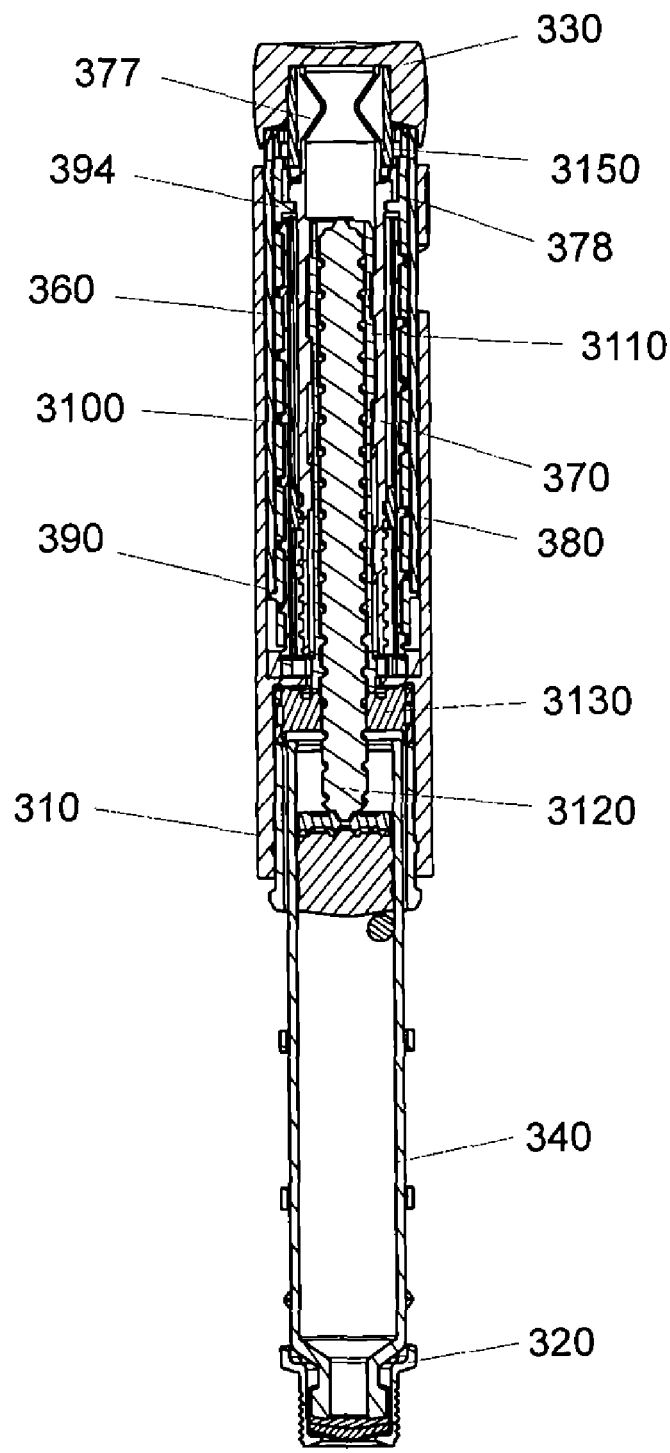
FIG. 10 shows a sectional view of the injection device of FIG. 9 with no dose set
Figure 11:
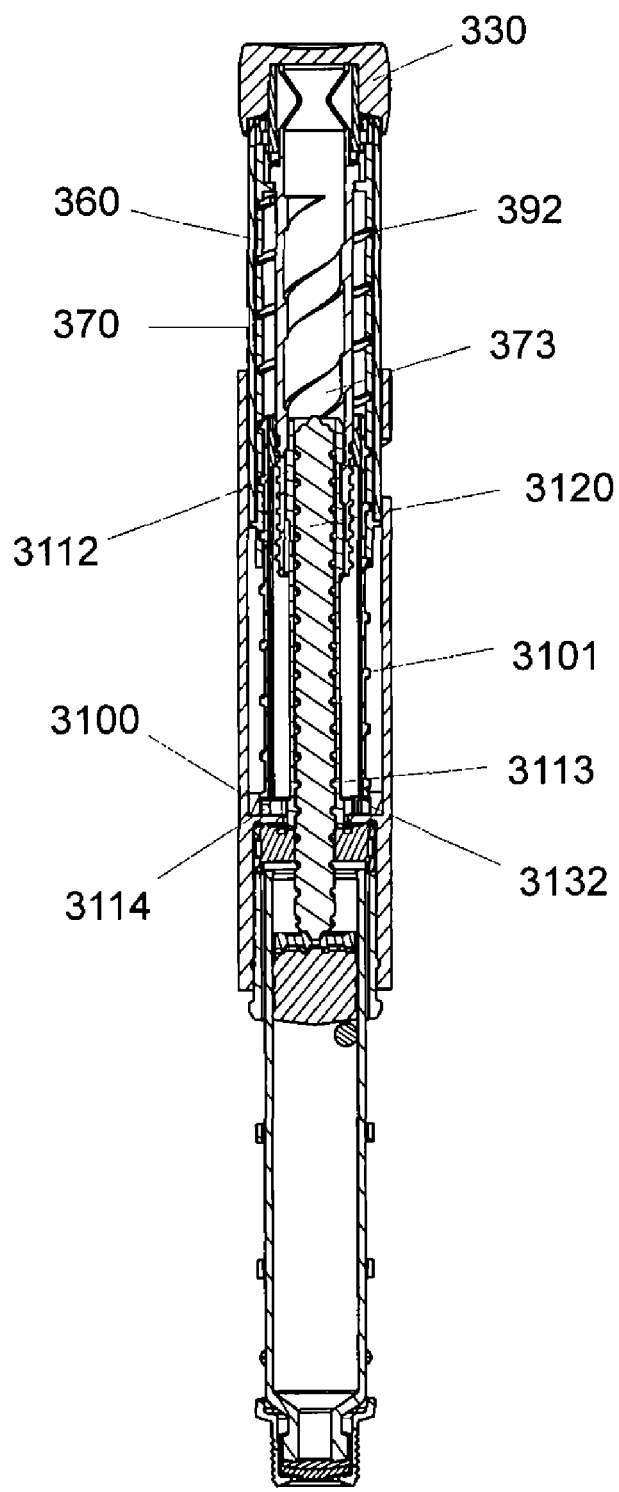
FIG. 11 shows a sectional view of the injection device of FIG. 9 with a dose set

Embodiment Disclosed in FIGS. 9 to 11

In this embodiment a dose is set by rotating the push button 330 which rotates the click element 3150. Due to engagement between the rim of teeth 3152 on the click element 3150 and the rim of teeth 391 on the inside surface of the dose indication sleeve 390 this is rotated with the push button 330.

The internal thread 392 is screwed up the thread 3101 provided on the thread member 3100 such that the dose indication sleeve 290 is lifted out from the housing 310. Due to the engagement between the rim 394 inside the dose indication sleeve 290 and the rim 378 on the drive sleeve 370, the drive sleeve 370 is also lifted in the proximal direction. During this axial movement of the drive sleeve 370 it is rotated on the thread 3112 provided on the piston rod guide 3110.

The thread member 3100 is locked to the housing 310 and the piston rod guide 3110 is coupled to the thread member 3100 via a one way coupling between the resilient pawls 3114 on the piston rod guide 3110 and the toothed ring 3132 inside the distal end of the thread member 3100.

When injecting the set dose, the user presses the push button 330 axially back towards the housing 310 against the force of the spring 377.

The push button 330 and the click member 3150 locks to the shield 360 which is guided in a longitudinal recess 312 in the housing 310. Further the drive sleeve 370 locks to the click member 3150 via the teeth 376 on the rim 378 engaging a rim of not shown teeth located distally on the click element 3150. This results in an axial movement of the push button 330, the click element 3150, the drive sleeve 370 and the shield 360.

The axial returning of the drive sleeve 370 forces the piston rod guide 110 to rotate due to the thread connection 3112, 373. The internal thread 3113 of the piston rod guide 3110 transforms rotation to the piston rod 3120 which is screwed forward in the keyed engagement with the dish 3130.

At the same time the teeth 3152 on the click element 3150 escapes the engagement with the protrusions 391 on the dose indication sleeve 390 which is then screwed down the thread 3101 on the thread member 3100 back to its zero position.

An End-of-Content nut 380 is provided between the drive sleeve 370 and the thread member 3100.

Figure 12:
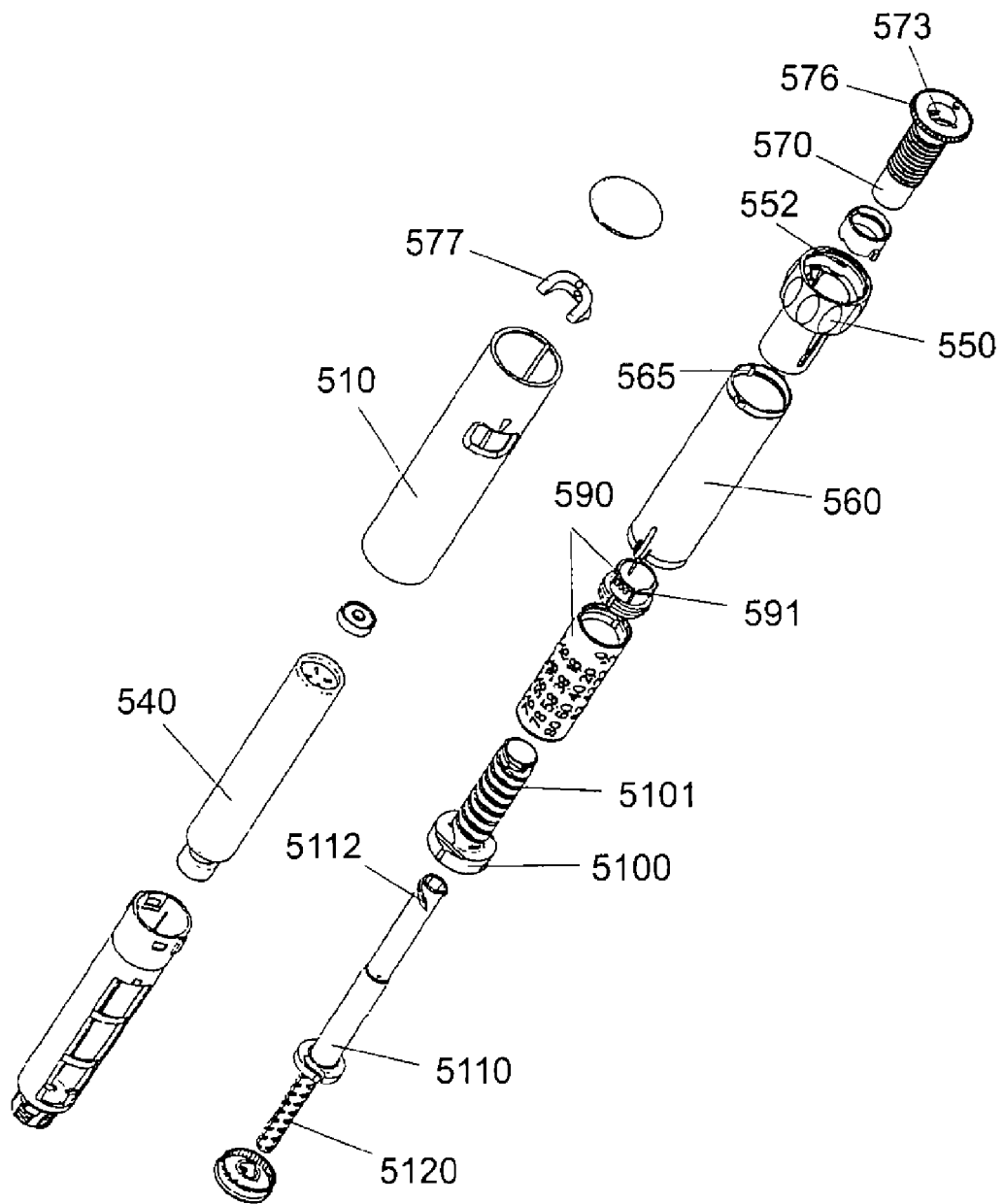
FIG. 12 shows a perspective view of another example of an injection device.
Figure 13:
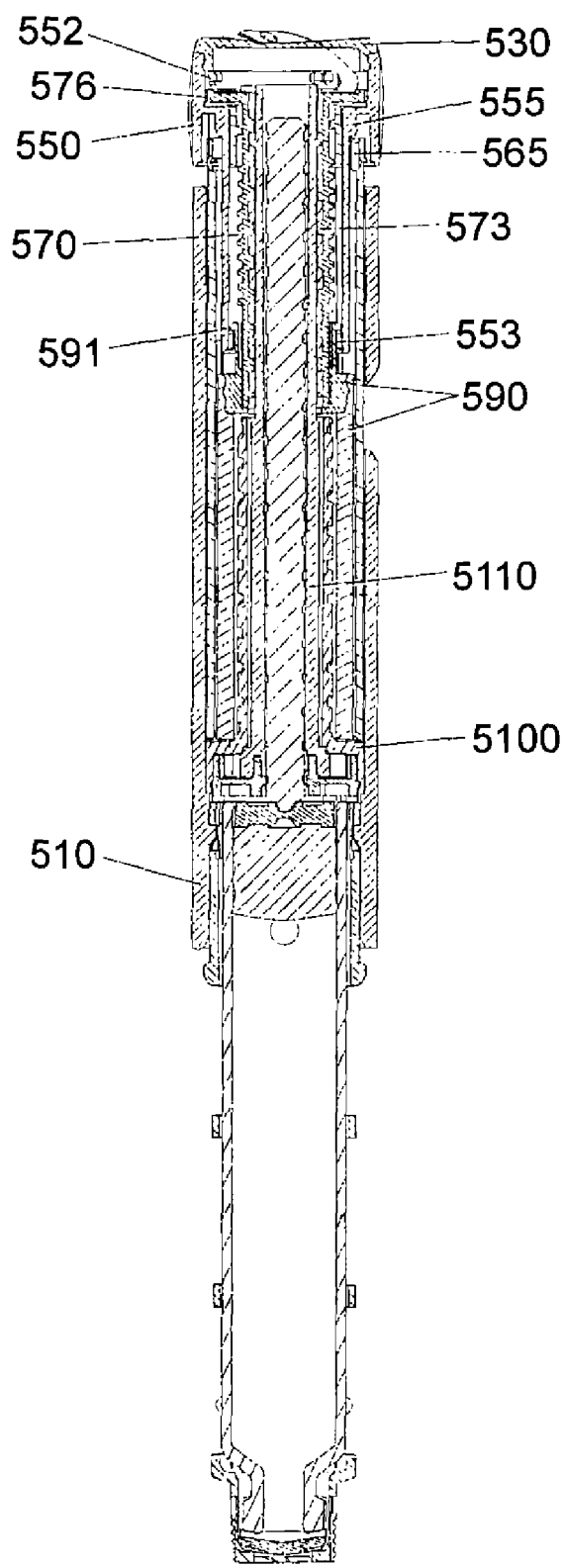
FIG. 13 shows a sectional view of the injection device of FIG. 13.

Embodiment Disclosed in FIG. 12-13

In this embodiment the dose is set by rotating the dose setting member 550. The dose setting member 550 has internal teeth 553 engaging sleeve rim 591 on the dose indicator sleeve 590. In the disclosed embodiment, the dose indication sleeve 590 is made up from two different parts which during assembly is connected in to one functional element. This element could however also be produced as one moulded element.

Once the user rotates the dose setting member 550, the dose indication sleeve 590 is lifted in the proximal direction by the thread 5101 on the thread member 5100 which is secured in the housing 510. During this proximal movement, the driver 570 will be lifted in the proximal during as it stands on the dose indication sleeve 590. The driver 570 has an internal thread 573 engaging the outwardly pointing thread 5112 on the piston rod guide 5110 and is thus forced to rotate on this thread 5112 when moved in the proximal direction. This thread 5112 has a pitch different from the pitch of the thread 5101 on the thread member 5100 accomplishing a gearing between the axial movement of the dose indication sleeve 590 and the driver 570.

When injecting the set dose, the user applies a pressure on the push button 530 which is secured in the dose setting member 550. This moves the dose setting member 550 axially in the distal direction thus releasing the teeth 553 from the toothed rim 591. The same axial movement also moves the teeth 552 on the dose setting member 550 into engagement with the proximal teeth 576 on the driver 570 which is biased away from the push button 530 by the spring element 577.

The dose setting member 550 locks to the shield 560 through the teeth connection 555/565. Since the shield 560 is guided in the track 512 in the housing 510, continuously movement of the dose setting member 550 in the distal direction will force the driver 570 axially forward. This axial forward movement of the driver 570 forces the piston rod guide 5110 to rotate in the thread connection 5112/573 between the driver 570 and the piston rod guide 5110.

The dose indication sleeve 590 is released from the dose setting member 550 as the teeth 553 moves free of the toothed rim 591. The dose indication sleeve 590 is therefore free to return to its zero position down the thread 5101 as it is forced in the distal direction by the continuous pressure on the push button 530.

At the end of stroke, the dose indication sleeve 590 is accelerated due to the fact that the thread 5101 on the thread member 5100 has a higher pitch on the last revolution. This acceleration can be felt by the user who is thus informed that the mechanism has reached the end of the dosing stroke.

Figure 14:
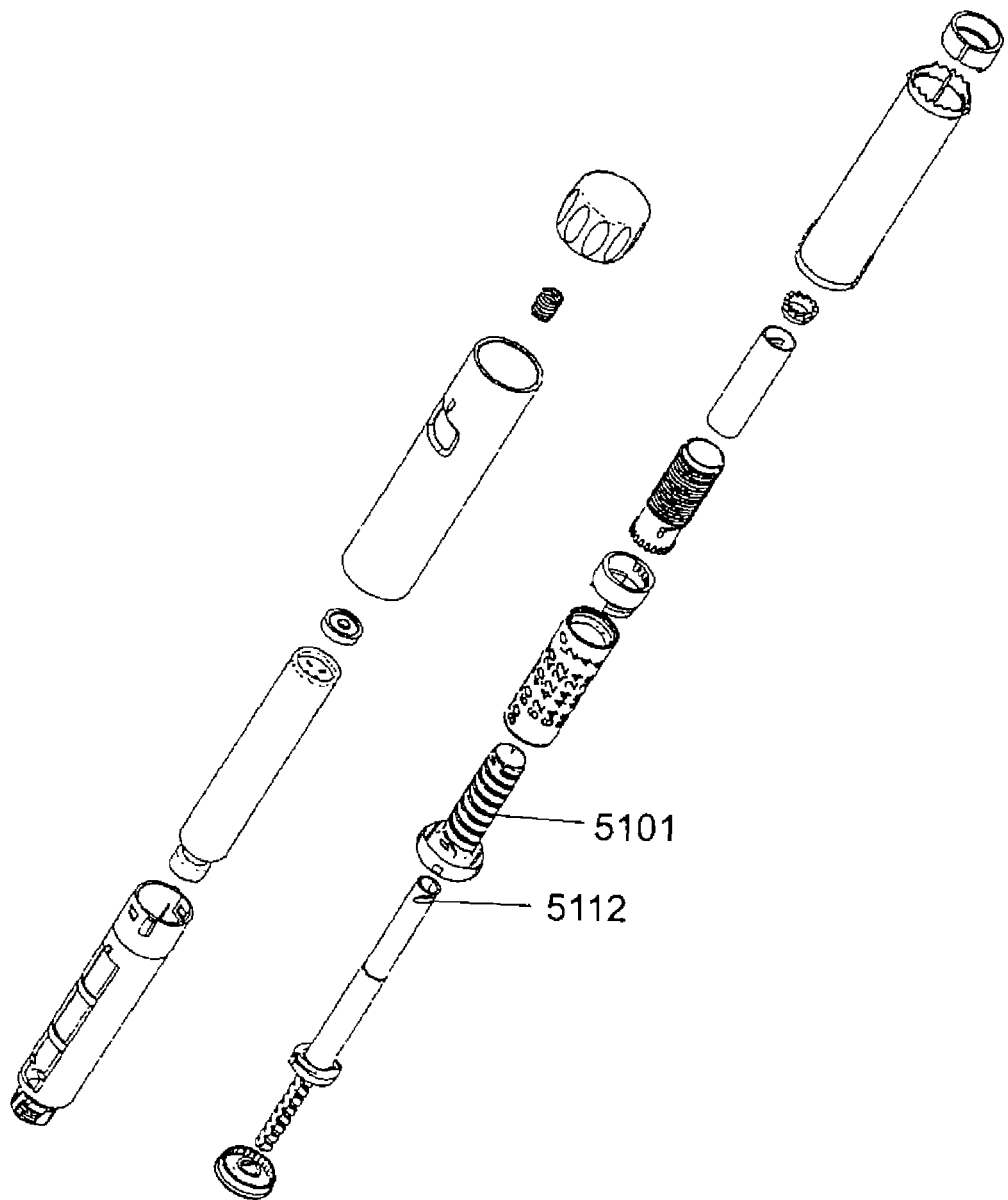
FIG. 14 shows a perspective view of an embodiment of the injection device disclosed in FIGS. 12 and 13.

Embodiment Disclosed in FIG. 14

If the two threads 5112, 5101 has different directions as disclosed in FIG. 14, the mechanism works in one direction when setting a dose and in the opposite direction when expelling the set dose.

Figure 15:
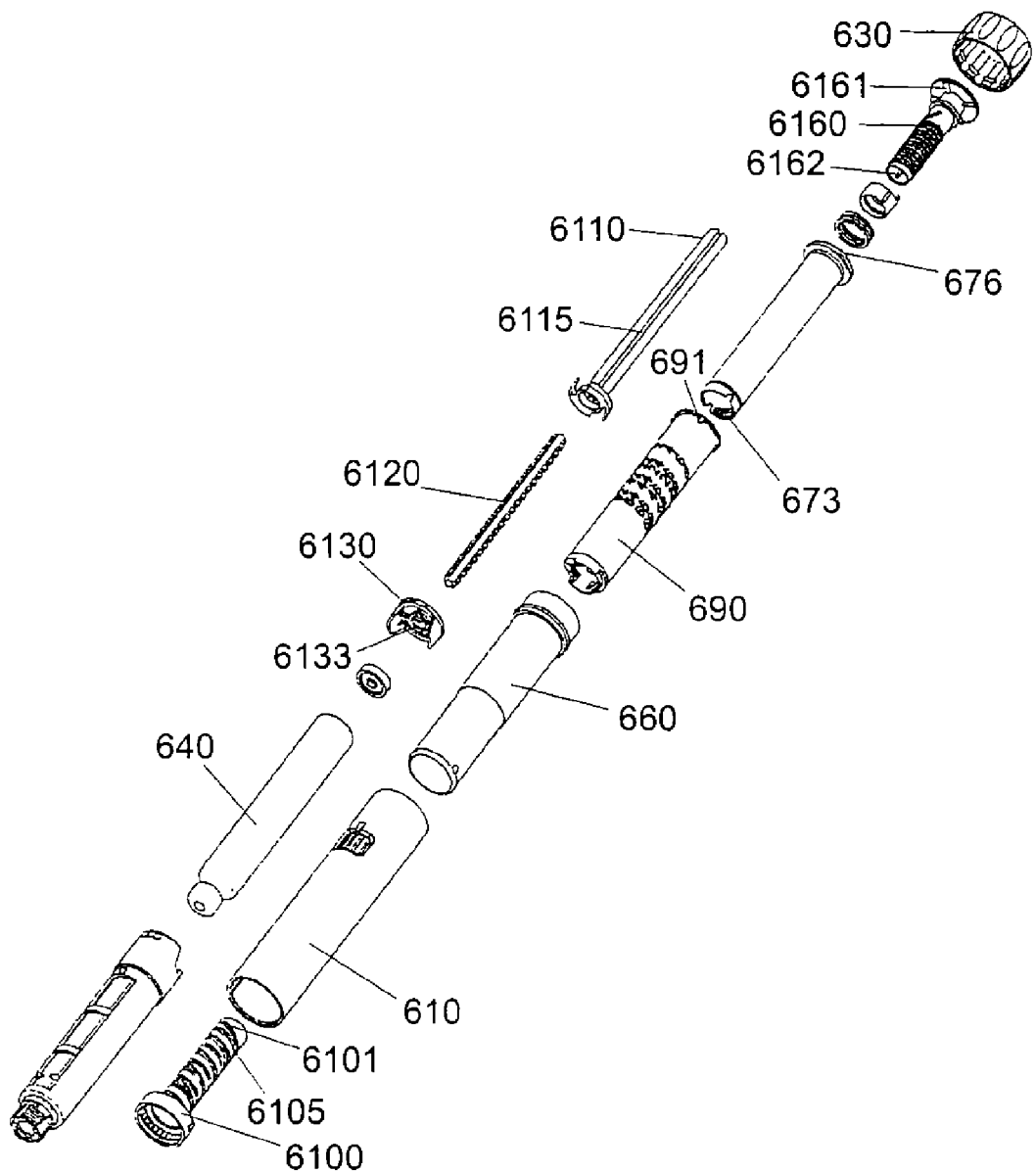
FIG. 15 shows a perspective view of another example of an injection device.
Figure 16:
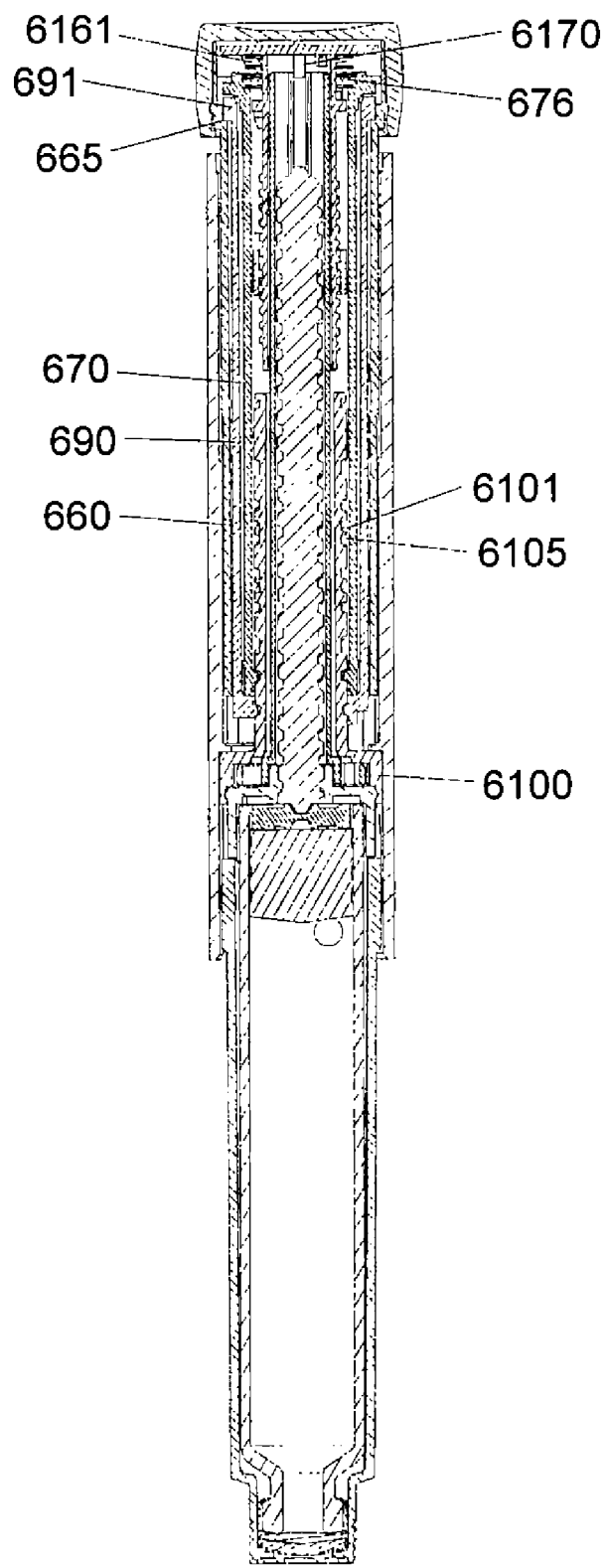
FIG. 16 shows a perspective view of the injection device according to FIG. 16

Embodiment Disclosed in FIG. 15-16

In the embodiment disclosed in FIG. 15-16 a dose is set by rotating the push button 630 which is connected to a transparent shield 660 such that the shield 660 rotates together with the push button 630. The shield 660 and the push button 630 could even be moulded as to form one common dose setting member.

The internal teeth 665 on the shield 660 engage the toothed rim 691 on the dose indicator sleeve 690 such that this sleeve 690 rotates together with the shield 660. During this rotation, the dose indication sleeve 690 is guided in the thread 6101 on the thread member 6100 which is secured in the housing 610.

The thread member 6100 has an additional thread 6105 in which the internal drive thread 673 of the driver 670 is guided as it is pulled in the proximal direction by the dose indication sleeve 690. This additional thread 6105 preferably has a pitch different form the pitch of the thread 6101 in which the dose indication sleeve 690 is guided such that a gearing between the scale indication sleeve 690 and the driver 670 is obtained.

In order to inject the set dose, the user applies a pressure on the push button 630. This pressure moves the push button 630 and the shield 660 in the distal direction thus releasing the teeth 665 on the shield 660 from the toothed ring 691 thereby releasing the dose indication sleeve 690 from the shield 660. At the same time the teeth 6161 on the connector pipe 6160 enters into engagement with the teeth 676 on the driver 670. As continuously pressure is applied to the push button 630, the driver 670 rotates down the thread 6105 on the thread member 6100. Since the connector pipe 6160 is now connected to the driver 670, the connector pipe 6160 also rotates. This rotation is through the connection between the internal protrusion 6162 on the connector pipe 6160 and the longitudinal track 6115 in the piston rod guide 6110 transformed to a rotation of the piston rod 6120 which is screwed forward in the internal thread 2133 in the dish or nut 2130.

This embodiment also discloses an End-of-Content indicator providing the user with a tactile indication once the end of the dosing stroke is reached. The mechanism comprises and EoD accelerator that is moved away from the proximal end of the piston rod guide 6110 as the dose is set. When the dose is injected, the EoD accelerator 6170 is moved towards the proximal end of the piston rod guide 6110. As it reaches the piston rod guide 6110, it is pressed radially outwardly by the piston rod guide 6110 due to the pressure applied to the push button 630. This is felt by the user as an increase in the pressure necessary. Once the EoD accelerator snaps over the end of the piston rod guide 6110, the user feels an decrease in the pressure necessary. This sudden decrease also accelerates the driver 670 which provides a distinct sound as the driver 670 accelerates into the dose indication sleeve 690 at its distal end.

Figure 17:
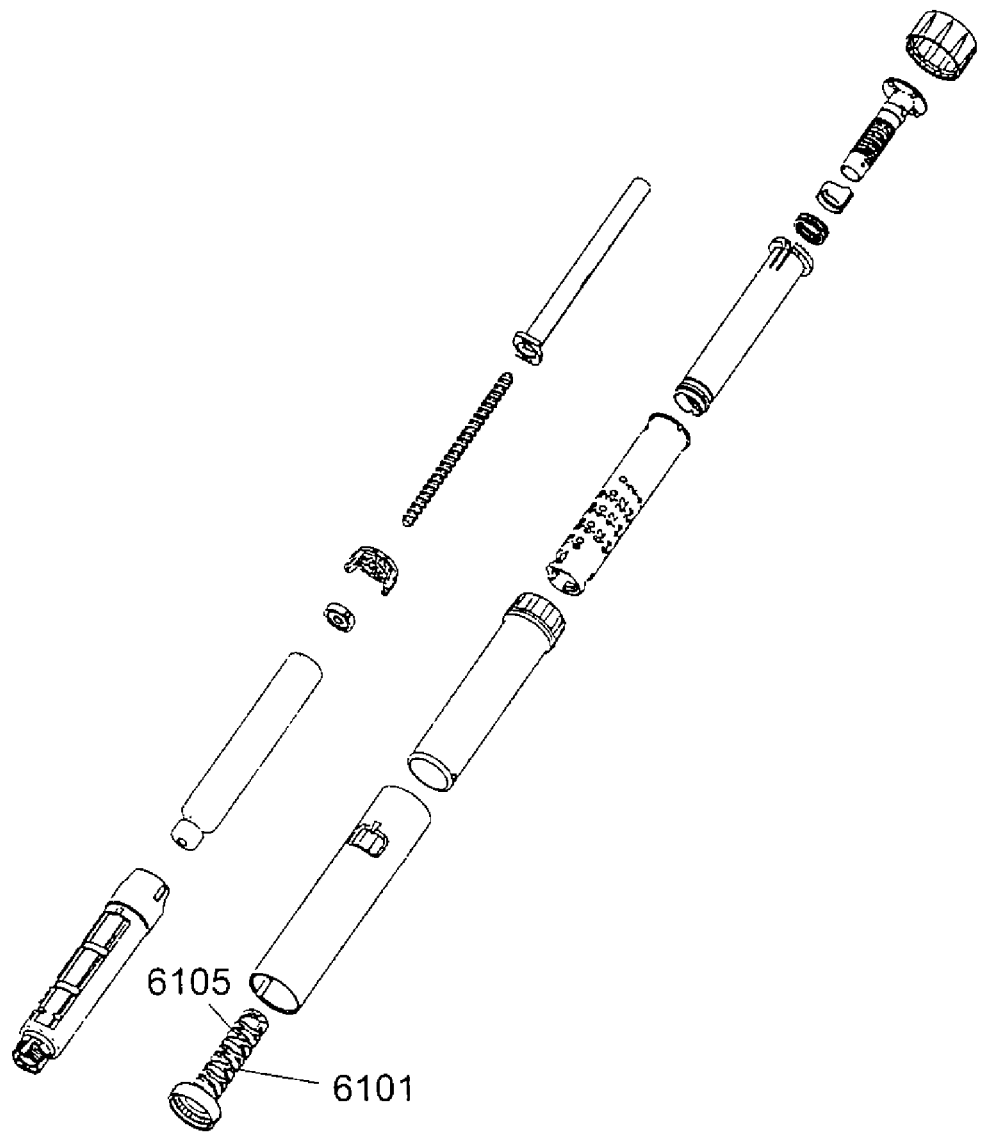
FIG. 17 shows a perspective view of an embodiment of the injection device disclosed in FIGS. 15 and 16.

Embodiment Disclosed in FIG. 17

If the two threads 6101, 6105 has different directions as disclosed in FIG. 17, the mechanism works in one direction when setting a dose and in the opposite direction when expelling the set dose.

Some preferred embodiments have been shown in the foregoing, but it should be stressed that the invention is not limited to these, but may be embodied in other ways within the subject matter defined in the following claims.

List of part:

| FIG. 1-5 | FIG. 6-8 | FIG. 9-11 | FIG. 12-14 | FIG. 15-17 | |
|---|---|---|---|---|---|
| 1 | 201 | 301 | | | Injection Pen |
| 10 | 210 | 310 | 510 | 610 | Housing |
| 11 | | | | | Window |
| 12 | 212 | | 512 | | Longitudinal Track |
| 20 | 220 | 320 | | | Cartridge Holder |
| 21 | | | | | Thread |
| 22 | | | | | Opening |
| 30 | 230 | 330 | | 630 | Push Button |
| 31 | | | | | Depression |
| 32 | | | | | Push Button Slits |
| | 233 | | | | Push Button Teeth |

-continued

List of part:

| FIG. 1-5 | FIG. 6-8 | FIG. 9-11 | FIG. 12-14 | FIG. 15-17 | |
|---|---|---|---|---|---|
| 40 | 240 | 340 | 540 | 640 | Cartridge |
| 50 | | | 550 | | Dose Setting Member |
| 51 | | | | | Locking Protrusion |
| 52 | | | 552 | | Toothed Rim |
| 53 | | | 553 | | Dose Setting Member Protrusions |
| 54 | | | | | EOC Thread |
| | | | 555 | | Teeth |
| 60 | 260 | 360 | | 660 | Shield |
| 61 | 261 | | | | Protrusion |
| 62 | | | | | Radial Shields Teeth |
| 63 | | | | | Longitudinal Slot |
| | 264 | | | | Toothed ring |
| | 265 | | 565 | 665 | Teeth |
| 70 | 270 | 370 | 570 | 670 | Driver |
| 71 | | | | | Resilient Arms |
| 72 | | | | | Toothed Surface |
| 73 | 273 | | 573 | | Internal Drive Thread |
| | 274 | | | | Ring Shaped Track |
| | 275 | | | | Helical Thread |
| | 276 | 376 | 576 | | Teeth |
| | 277 | 377 | 577 | | Spring |
| | | 378 | | | Rim |
| 80 | | 380 | | | EOC Nut |
| 81 | | | | | Internal Thread |
| 82 | | | | | Protrusion |
| 90 | 290 | 390 | 590 | 690 | Dose Indication Sleeve |
| 91 | 291 | 391 | 591 | 691 | Dose Indication Sleeve Rim |
| 92 | | 392 | | | Interior Thread |
| 93 | | | | | Mounting Opening |
| | 294 | | | | Inner Ring Shaped Protrusion |
| | 295 | | | | Outer Ring Shaped Protrusion |
| 100 | 2100 | 3100 | 5100 | 6100 | Thread Member |
| 101 | 2101 | 3101 | 5101 | 6101 | Thread |
| 102 | | | | | Thread Member Protrusion |
| | 2103 | | | | Toothed Ring |
| | 2104 | | | | Longitudinal Track |
| | | | | 6105 | Additional Thread |
| 110 | | 3110 | 5110 | 6110 | Piston Rod Guide |
| 111 | | | | | Outer Surface |
| 112 | | | 5112 | | Thread |
| 113 | | | | | Internal Thread |
| 114 | | | | | Pawls |
| 120 | 2120 | 3120 | | 6120 | Piston Rod |
| 121 | 2121 | | | | Key |
| 122 | | | | | Piston Rod Thread |
| 123 | | | | | Piston Foot |
| | 2124 | | | | Proximal Thread |
| 130 | 2130 | 3130 | | 6130 | Dish |
| 131 | | | | | Keyed Opening |
| 132 | | 3132 | | | Inwardly Pointing Teeth |
| | 2133 | | | 6133 | Internal Thread |
| | 2140 | | | | Key Element |
| | 2141 | | | | Key |
| | 2142 | | | | Resilient Arm |
| | 2150 | 3150 | | | Click Element |
| | 2151 | | | | Resilient Arm |
| | 2152 | 3152 | | | Toothed Ring |
| | | | | 6160 | Connector Pipe |
| | | | | 6161 | Teeth |
| | | | | 6162 | Internal Protrusion |
| | | | | 6170 | EoD Accelerator |

We claim:

1. An injection device for apportioning set doses of a drug from a reservoir comprising:
a housing (10, 210, 310, 510, 610) adapted to hold the reservoir (40, 240, 340, 540, 640),
a dose setting member (30, 50, 230, 2150, 330, 3150, 550, 630, 660) for setting the size of the dose to be expelled,
a scale indication sleeve (90, 290, 390, 590, 690) having numbers for indicating the size of the set dose,
a piston rod (120, 2120, 3120, 5120, 6120) for activating the reservoir (40, 240, 340, 540, 640) to expel the set dose,
a drive sleeve (70, 270, 370, 570, 670) associated with the piston rod (120, 2120, 3120, 5120, 6120) for driving the piston rod (120, 2120, 3120, 5120, 6120) forward,
wherein,
the scale indication sleeve (90, 290, 390, 590, 690) is surrounded by an axially slideable non-rotating shield (60, 260, 360, 560, 660) through which at least a portion of the numbers on the scale indication sleeve (90, 290, 390, 590, 690) are visible, wherein the shield moves relative to the housing during ejection of a dose of medication from the reservoir and wherein the numbers can be seen rotating.

\* \* \* \* \*